(12) United States Patent
Tobien (10) Patent No.: US 10,758,647 B2
(45) Date of Patent: Sep. 1, 2020

(54) MEDICAL PUSH BUTTON VALVE

(71) Applicant: KARL STORZ SE & Co. KG, Tuttlingen (DE)

(72) Inventor: Johannes Peter Tobien, Tuttlingen (DE)

(73) Assignee: KARL STORZ SE & Co. KG, Tuttlingen (DE)

(*) Notice: Subject to any disclaimer, the term of this patent is extended or adjusted under 35 U.S.C. 154(b) by 18 days.

(21) Appl. No.: 16/010,924

(22) Filed: Jun. 18, 2018

(65) Prior Publication Data

US 2018/0361034 A1  Dec. 20, 2018

(30) Foreign Application Priority Data

Jun. 16, 2017  (DE) .......................... 10 2017 005 718

(51) Int. Cl.
*F16K 31/528* (2006.01)
*A61M 1/00* (2006.01)
(Continued)

(52) U.S. Cl.
CPC ....... *A61M 1/0035* (2014.02); *A61B 1/00068* (2013.01); *A61M 1/0043* (2013.01); *A61M 39/22* (2013.01); *A61M 39/24* (2013.01); *F16K 3/24* (2013.01); *A61M 5/16813* (2013.01); *A61M 39/225* (2013.01); *A61M 2039/226* (2013.01); *A61M 2039/2473* (2013.01);
(Continued)

(58) Field of Classification Search
CPC .. A61M 1/0035; A61M 1/0043; A61M 39/22; A61M 39/24; F16K 3/24; F16K 31/528; F16K 31/5286; F16K 31/60; F16K 1/12
USPC .................................. 251/319, 321, 323, 229
See application file for complete search history.

(56) References Cited

U.S. PATENT DOCUMENTS 1,463,735 A * 7/1923 Varrieur ................. B67D 3/043
251/100
2,606,736 A * 8/1952 Ferm ....................... F01B 17/02
251/76
(Continued)

FOREIGN PATENT DOCUMENTS

DE         20020298 U1    4/2001
DE     102005029756 A1    1/2007
(Continued)

*Primary Examiner* — Kelsey E Cary
(74) *Attorney, Agent, or Firm* — Muncy, Geissler, Olds & Lowe, P.C.

(57) ABSTRACT

A medical push button valve having a valve housing, a flow channel formed in the valve housing as well as a valve piston which is arranged displaceably in the valve housing between a position releasing the flow channel and a position closing the flow channel. The valve piston is operatively connected with a pressure element mounted on the valve housing and is spring-loaded via at least one spring element. The valve piston is biased into the position closing the flow channel with the spring-loaded pressure element. In order to provide a medical push button valve which allows for a simple and fatigue-free one-handed operation, the spring-loaded pressure element can be locked in at least one position in which the valve piston operatively connected with the pressure element at least partially releases the flow channel.

9 Claims, 7 Drawing Sheets

(51) Int. Cl.
  *A61M 39/22* (2006.01)
  *A61M 39/24* (2006.01)
  *A61B 1/00* (2006.01)
  *F16K 3/24* (2006.01)
  *F16K 11/07* (2006.01)
  *A61M 5/168* (2006.01)

(52) U.S. Cl.
  CPC ...... *A61M 2039/2493* (2013.01); *F16K 11/07* (2013.01); *F16K 31/5286* (2013.01)

(56) References Cited

U.S. PATENT DOCUMENTS

| | | | | |
|---|---|---|---|---|
| 5,228,646 A | * | 7/1993 | Raines | A61M 39/22 |
| | | | | 251/322 |
| 5,364,070 A | * | 11/1994 | Crow | F16K 31/44 |
| | | | | 251/322 |
| 5,427,144 A | | 6/1995 | Teets et al. | |
| 5,433,410 A | * | 7/1995 | Foltz | F01M 11/0408 |
| | | | | 251/100 |
| 6,364,853 B1 | | 4/2002 | French et al. | |
| 7,484,709 B2 | | 2/2009 | Efinger et al. | |
| 8,235,889 B2 | | 8/2012 | Kohno | |
| 2007/0007479 A1 | * | 1/2007 | Efinger | A61M 1/0043 |
| | | | | 251/149.9 |
| 2011/0233439 A1 | * | 9/2011 | Lee | F16K 31/60 |
| | | | | 251/319 |
| 2016/0081538 A1 | | 3/2016 | Rebholz et al. | |
| 2016/0361082 A1 | * | 12/2016 | Brommersma | A61M 39/22 |

FOREIGN PATENT DOCUMENTS

| | | |
|---|---|---|
| DE | 102016216023 A1 | 3/2018 |
| EP | 1707107 A1 | 10/2006 |
| EP | 2431062 A1 | 3/2012 |
| EP | 2997876 A1 | 3/2016 |
| JP | H1052399 A | 2/1998 |

* cited by examiner

MEDICAL PUSH BUTTON VALVE

This nonprovisional application claims priority under 35 U.S.C. § 119(a) to German Patent Application No. 10 2017 005 718.4, which was filed in Germany on Jun. 16, 2017, and which is herein incorporated by reference.

BACKGROUND OF THE INVENTION

Field of the Invention

The present invention relates to a medical push button valve, having a valve housing, a flow channel formed in the valve housing and a valve piston which is disposed displaceably in the valve housing between a position releasing the flow channel and a position closing the flow channel, wherein the valve piston is operatively connected with a pressure element mounted on the valve housing and spring-loaded via at least one spring element, and the valve piston is biased by the spring-loaded pressure element in the position closing the flow channel.

Description of the Background Art

During surgical operations, it is often necessary to aspirate fluids such as blood or rinsing solution from the operation site. For this purpose, surgical instruments equipped with a suction channel can be connected to an external suction source, for example a vacuum pump, via a preferably flexible suction line.

Since the power of the vacuum pump generating the suction flow is usually not adjustable in the operating room, it is common to equip the medical instruments, such as endoscopes, with a valve via which the suction flow can be switched on or off.

From practice, it is known to configure such a valve for closing and/or switching off the suction flow as a push button valve in which the valve body releasing or closing the flow channel is actuatable via a spring-loaded pressure element, wherein the valve body is biased by a spring element in the position closing the flow channel.

These known push button valves, in which the surgeon must press the spring-loaded pressure element to release the flow channel, have proven themselves in practice. A disadvantage of this known design of the push button valve is that the surgeon must keep the spring-loaded pressure element pressed during the entire suction process since the valve body is biased into the position closing the suction channel.

For some examinations and/or treatments, such as of the bile duct, it is necessary to ensure continuous suction to prevent leakage of secretions from another working channel inlets. The permanent pressing of the spring-loaded pressure element to ensure continuous suction is strenuous for the surgeon and can lead to cramping of the finger due to the constant holding position.

SUMMARY OF THE INVENTION

It is therefore an object of the present invention to provide a medical push button valve which allows for simple and fatigue-free one-handed operation.

In an exemplary embodiment, a spring-loaded pressure element can be locked in at least one position in which the valve piston operatively connected with the pressure element at least partially releases the flow channel.

By forming the at least one locking position of the pressure element in a position in which the valve body at least partially releases the flow channel, the surgeon is freed from the permanent depression of the pressure element known from practice, thereby providing significant relief for the holding hand of the surgeon.

The spring-loaded pressure element can be locked only in the position in which the valve piston operatively connected with the pressure element completely releases the flow channel. In this locked position of the pressure element or the valve piston operatively connected thereto, the full suction power is applied to the distal end of the valve housing leading to the patient.

The spring-loaded pressure element can be mounted in a pusher housing arranged at the proximal end of the valve housing, wherein the spring-loaded pressure element is rotatable relative to the pusher housing about the longitudinal axis of the valve housing.

To form the locking function of the spring-loaded pressure element, the invention proposes that the spring-loaded pressure element and the pusher housing are coupled to one another via a pin and slot control. The pin and slot control allows for guided displacement of a pin formed on a component in a kind of slotted guide, which is formed on the other component, wherein it is irrelevant to the mechanism on which of the components the pressure element or pusher housing of the pins or the guide for the pins is formed.

The pin and slot control can be designed as a bayonet lock. The bayonet lock with a one-sided angled longitudinal slot and a pin guided in the longitudinal slot is characterized by its ease of manufacture and ease of use. By simply pressing and twisting one of the two components relative to the other component, the bayonet lock can be operated quickly with just one hand.

Advantageously, two bayonet locks offset by 180° from one another are provided on the pusher housing in order to ensure a tilt-free actuation. Depending on the size of the pusher housing, more than two bayonet locks, such as three bayonet locks arranged offset from each other by 120°, can be used.

The pin and slot control can also be designed as a groove and a latching surface, wherein in the locking position, the groove formed on the rotatable pressure element receives the latching surface formed on the pusher housing.

To form the spring element acting on the pressure element, the at least one spring element can be spring-loaded via the pressure element, and can be formed integrally with the pressure element or the pusher housing, wherein the spring elasticity of the material from which the pressure element or the pusher housing are made is used to form the spring property.

Furthermore, when viewed in the direction of the longitudinal axis of the valve housing, two sealing bodies which cooperate with corresponding valve seats can be formed on the valve piston at a distance from each other. While the one sealing body with its associated valve seats serves to seal the pusher housing with respect to the ambient air, the flow channel can be closed on the patient side by means of the other sealing body with its associated valve seat.

The sealing bodies of the valve piston are inventively designed as a thickening of the valve piston with conical transition areas. The conical design of the sealing body prevents the flow channel from being suddenly closed or opened when adjusting the valve piston. Due to the conicity of the sealing body, a slow opening and closing of the flow channel is possible.

In a transition region from the valve housing to the pusher housing on the outside of the two housings, an elastic locking ring interconnecting the two housings is arranged.

This way of connecting the two housings via the elastic locking ring represents a particularly simple type of assembly and disassembly which is quickly performed.

In order to enable a particularly simple operation of the spring-loaded pressure element with only one hand or even a single finger, the invention proposes that at the proximal end of the spring-loaded pressure element, a radially outwardly projecting actuating lever is arranged. Via the actuating lever, the spring-loaded pressure element can easily rotate to accomplish the locking via the pin and slot control.

Further, grip recesses can be formed in the outer contour of the proximal end of the spring-loaded pressure element.

Further scope of applicability of the present invention will become apparent from the detailed description given hereinafter. However, it should be understood that the detailed description and specific examples, while indicating preferred embodiments of the invention, are given by way of illustration only, since various changes, combinations, and modifications within the spirit and scope of the invention will become apparent to those skilled in the art from this detailed description.

BRIEF DESCRIPTION OF THE DRAWINGS

The present invention will become more fully understood from the detailed description given hereinbelow and the accompanying drawings which are given by way of illustration only, and thus, are not limitive of the present invention, and wherein:

FIG. 1b is a longitudinal section along the line Ib-Ib according to FIG. 1a;

FIG. 2b is a longitudinal section along the line IIb-IIb according to FIG. 2a;

FIG. 3b is a longitudinal section along the line IIIb-IIIb according to FIG. 3a;

FIG. 5b is a longitudinal section along the line Vb-Vb according to FIG. 5a;

FIG. 5c is a cross section along the line Vc-Vc according to FIG. 5a;

FIG. 6b is a longitudinal section along the line VIb-VIb according to FIG. 6a;

FIG. 6c is a cross section along the line VIc-VIc according to FIG. 6a;

FIG. 7b is a longitudinal section along the line VIIb-VIIb according to FIG. 7a;

FIG. 7c is a cross section along the line VIIc-VIIc according to FIG. 7a;

FIG. 8b is a longitudinal section along the line VIIIb-VIIIb according to FIG. 8a; and FIG. 8c is a cross section along the line VIIIc-VIIIc according to FIG. 8a.

DETAILED DESCRIPTION

FIGS. 1a to 3b and FIGS. 5a to 8c show a medical push button valve 1 which are formed of a valve housing 2, a flow channel 3 formed in the valve housing 2 and a valve piston 4 which is arranged displaceably in the valve housing 2 between a position releasing the flow channel 3 and a position closing the flow channel 3.

Figure 1A:
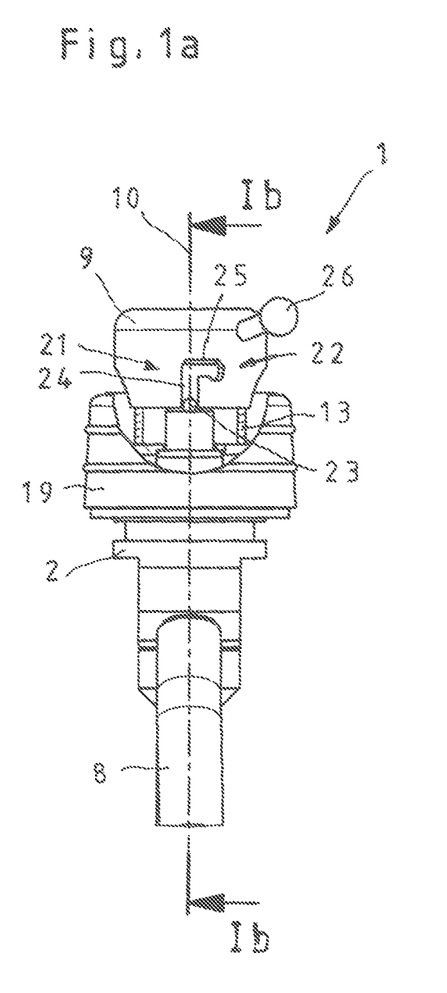
FIG. 1a is a partially cutaway side view of a first embodiment of a push button valve according to the invention, illustrating the valve in the position closing the flow channel.
Figure 1B:
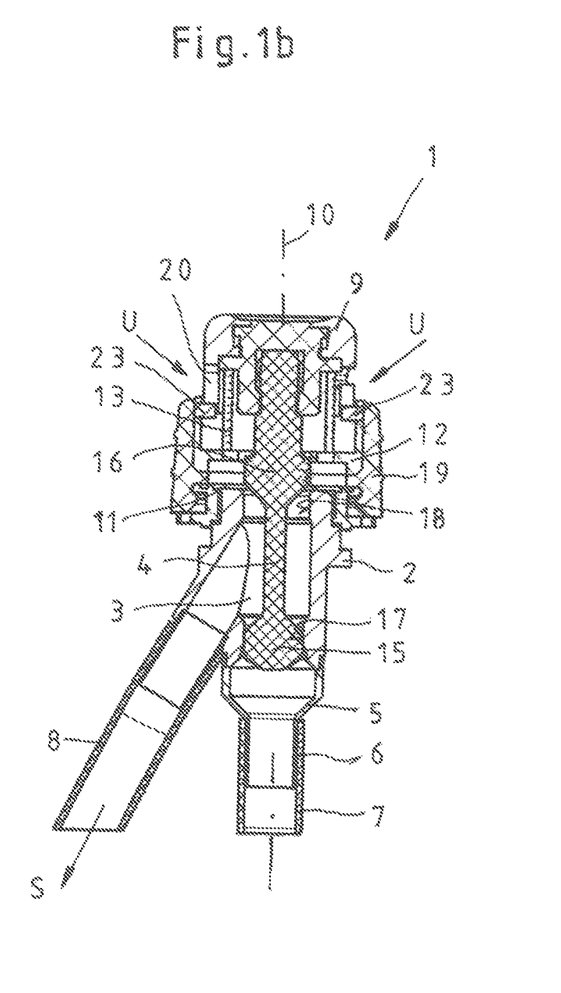
Figure 2A:
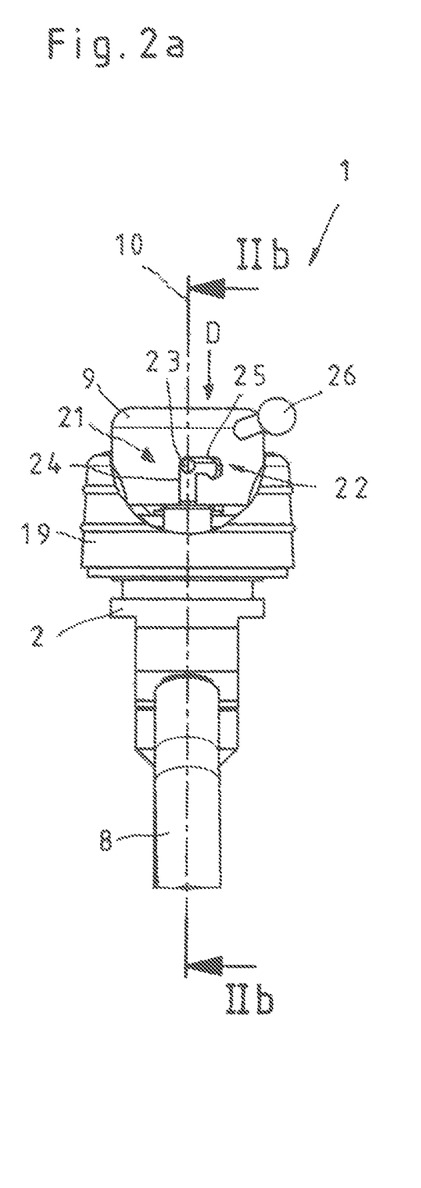
FIG. 2a is a view according to FIG. 1a, but illustrating the valve in a position releasing the flow channel.
Figure 2B:
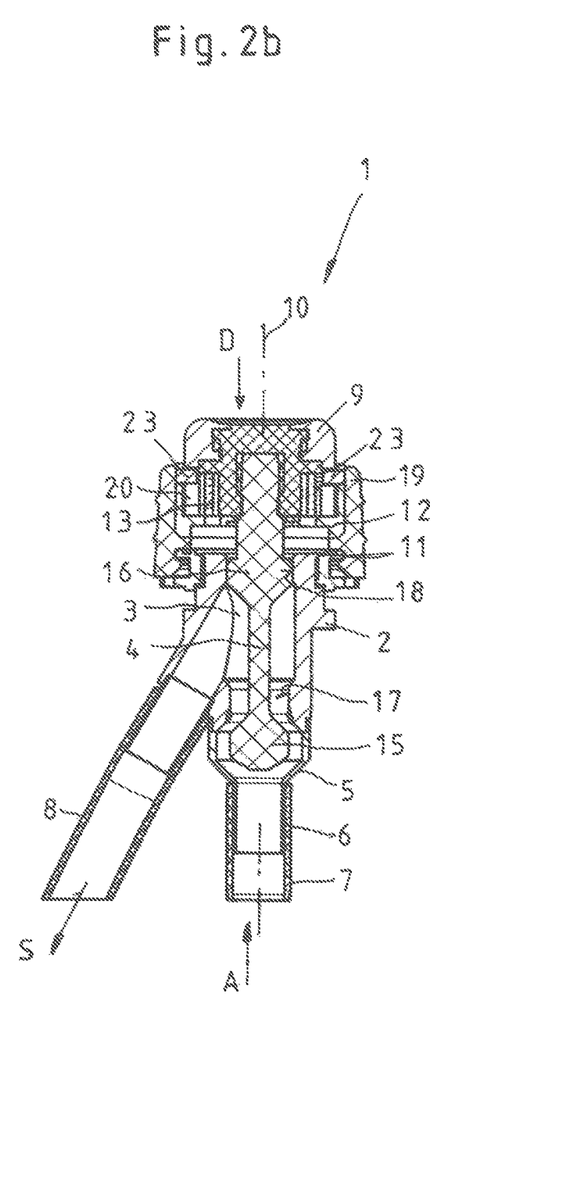
Figure 3A:
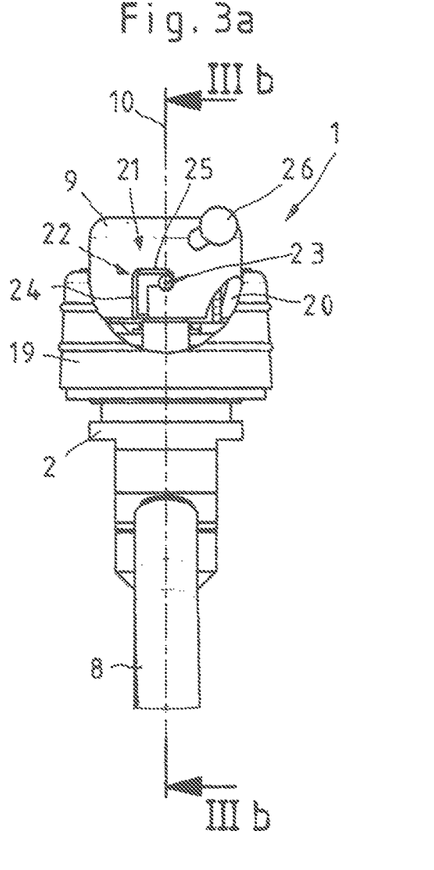
FIG. 3a is a view according to FIG. 2a, but additionally showing the pressure element in a locked position.
Figure 3B:
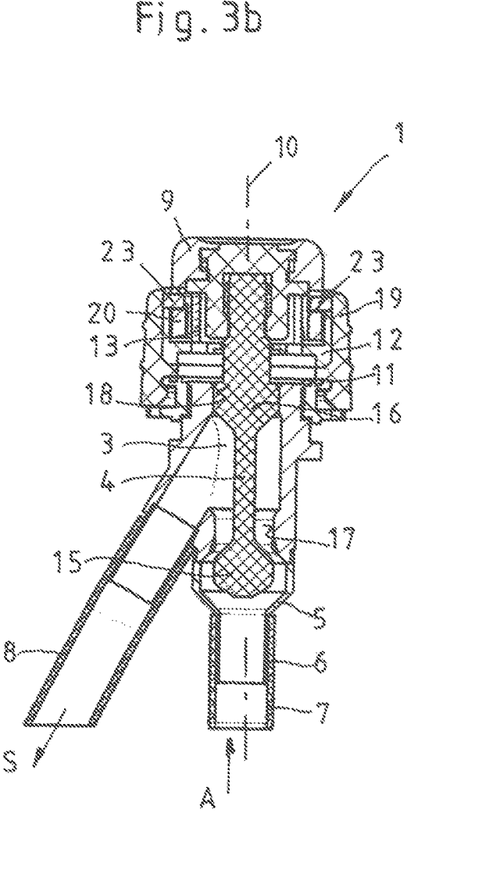

As can be seen from the sectional side views according to FIGS. 1b, 2b and 3b, a connecting piece 6 is arranged at the distal end 5 of the valve housing 2, via which the push button valve 1 can be connected to a line 7 leading to the patient.

With the suction power coming from an external suction source, the push button valve 1 is acted upon via a suction line 8, which opens laterally into the valve housing 2 at an acute angle.

The adjustment of the valve piston 4 between the position releasing the flow channel 3 and the position closing the flow channel 3 takes place via a pressure element 9, which is mounted axially displaceable in the direction of the longitudinal axis 10 of the valve housing 2 in a pusher housing 12 which is arranged at the proximal end of the valve housing 11. Furthermore, the pressure element 9 is rotatable relative to the pusher housing 12 about the longitudinal axis 10 of the valve housing 2.

The interaction between the pressure element 9 and the valve piston 4 is designed such that the valve piston 4 is biased into the position closing the flow channel 3 by a spring element 13 acting on the pressure element 9. This means that to open the flow channel 3, the pressure element 9 must be pressed distally against the force of the spring element 13 in the direction of the longitudinal axis 10 of the valve housing 2 to transfer the valve piston 4 into the position releasing the flow channel 3.

As an alternative to the illustrated design of the spring element 13 as a helical compression spring, it is also possible to form the spring element, spring-loaded via the pressure element 9, integrally with the pressure element 9 or with the pusher housing 12, wherein the spring elasticity of the material from which the pressure element 9 and the pusher housing 12 are made, is used to form the spring property.

As can be seen, for example, from the illustration in FIG. 1b, viewed in the direction of the longitudinal axis 10 of the valve housing 2, two sealing bodies 15 and 16 are formed at a distance from one another on the valve piston 4, which cooperate with corresponding valve seats 17 and 18. The operation of the two sealing bodies 15 and 16 and the two valve seats 17 and 18 will be described below in the description of the operation of the push button valve 1.

Figure 4:
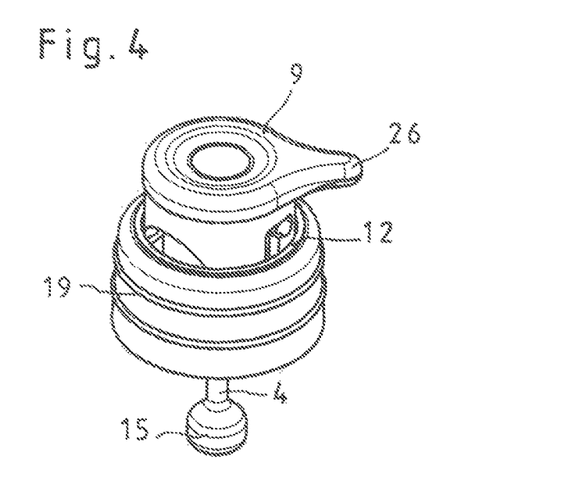
FIG. 4 is a perspective view of the pusher housing disassembled from the valve housing, including the valve piston.

In the transition region from the valve housing 2 to the pusher housing 12, an elastic locking ring 19 is arranged on the outside of the two housings 2 and 12, which, fixed to the pusher housing 12, serves to connect the pusher housing 12 to the valve housing 2. FIG. 4 shows the pusher housing 12 disassembled from the valve housing 2. For mounting to the valve housing 2, the elastic locking ring 19 connected to the pusher housing 12 is slipped over the upper part of the valve housing 2, thus connecting the two housings 2 and 12 to each other.

For cleaning purposes, the pusher housing 12 and the valve housing 2 can advantageously be separated from each other, wherein the valve piston 4 together with the pusher housing 12 can be withdrawn proximally from the valve housing 2, as shown in FIG. 4.

The operation of the medical push button valve 1 will be described below with reference to the drawings FIGS. 1a to 3b.

The sectional view of the push button valve 1 shown in FIG. 1b shows the unactuated starting position of the push button valve 1, in which the valve piston 4 completely closes the flow channel 3 formed in the valve housing 2 at the distal end. In this closed position, the sealing body 15 arranged on the end of the valve piston 4 remote from the pressure element 9 radially circumferentially seals against the valve seat 17 formed in the valve housing 2 and thus closes the flow channel 3 in a substantially fluid-tight manner.

By way of the spring element 13 supported on one side on the pusher housing 12, the pressure element 9, which is formed in two parts in the first embodiment shown in FIGS. 1a to 3b, is moved proximally in the direction of the longitudinal axis 10 of the valve housing 2 (in the illustration FIG. 1b, upwards).

Since in the operating room, the power of the vacuum pump generating the suction flow is usually not adjustable, i.e., even in the closed position of the valve piston 4, a permanent suction flow is present on the push button valve 1 via the suction line 8 in the direction of the arrow S, air intakes 20 are formed in the pusher housing 12 via which ambient air can be drawn in the direction of the arrow U and discharged via the suction line 8. The ambient air U drawn in via the air intakes 20 prevents negative pressure from forming in the valve housing 2 due to the permanent suction through the suction line 8, which on the one hand would strongly stress sealing elements in the push button valve 1 and on the other hand, could possibly complicate the actuation of the valve piston 4.

As can be seen in particular from FIGS. 1a, 2a and 3a, the spring-loaded pressure element 9 and the pusher housing 12 are coupled to one another via a pin and slot control 21, which in the illustrated first embodiment is designed as a bayonet lock 22 with a locking pin 23 and a slotted guide 24.

The illustrated pin and slot control 21 formed of two bayonet locks 22 arranged offset by 180 degrees to each other over the circumference of the pusher housing 12. FIGS. 1b, 2b and 3b show the two locking pins 23 of the bayonet locks 22. By using two bayonet locks 22, tilt-free operation of the pin and slot control 21 is ensured.

As an alternative to the use of two bayonet locks 22 offset by 180°, depending on the circumference of the pusher housing 12, more than two bayonet locks 22, such as three bayonet locks 22 offset by 120° to each other, may be used.

In the position of the push button valve 1 shown in FIG. 1a, in which the valve piston 4 is in the position closing off the flow channel 3, the locking pin 23 is arranged at the lower end of the slotted guide 24.

The sectional view of the push button valve 1 shown in FIG. 2b shows the actuated position of the push button valve 1, in which the valve piston 4 completely releases the flow channel 3 formed in the valve housing 2 at the distal end. In this open position, the sealing body 15 of the valve piston 4 is no longer sealingly attached to the valve seat 17 formed in the valve housing 2, but is displaced towards the distal in the direction of the longitudinal axis 10 of the valve housing 2, away from the valve seat 17 (in FIG. 2b, downwards).

Adjusting the valve piston 4 from the position closing the flow channel 3 shown in FIG. 1b into the position releasing the flow channel 3 shown in FIG. 2b is effected by pressing the spring-loaded pressure element 9 in the direction of the longitudinal axis 10 of the valve housing 2 towards the distal (in FIG. 2b, downwards) by means of a compressive force D. The axial pressure movement of the pressure element 9 is transmitted without play to the valve piston 4, whereby the sealing body 15 is pressed out of the sealing engagement with the valve seat 17.

In this open position of the flow channel 3, the influx of ambient air U through the air intakes 20 is sealed off by the second sealing body 16 of the valve piston 4 arranged close to the pressure element 9, since with a depressed pressure element 9, this sealing body 16 radially circumferentially sealingly abuts the corresponding second valve seat 18 formed in the valve housing 2.

Closing the influx of the ambient air U shown in FIG. 1b allows for the full suction power of the suction line 8 to be present at the flow channel 3 and for liquid to be aspirated from the patient through the line 7 in the direction of the suction direction A indicated by the arrow.

In the position of the push button valve 1 shown in FIG. 2a, in which the valve piston 4 is in the position releasing the flow channel 3, the locking pin 23 is arranged at the upper vertical end of the slotted guide 24.

Since the spring element 13 is arranged such that the pressure element 9 and thus also the valve piston 4 are biased into the position closing off the flow channel 3, the surgeon must hold the pressure element 9 with the compressive force D pressed down as long as the suction pressure is to bear against the line 7.

In order to relieve the surgeon, according to the position of the push button valve 1 shown in FIGS. 3a and 3b, it is possible to lock the pressure element 9 and thus also the valve piston 4 operatively connected with the pressure element 9 in the position releasing the flow channel 3.

For this purpose, the slotted guide 24 has a right-angled bend 25 at its upper end. Since the pressure element 9 is rotatable relative to the pusher housing 12 about the longitudinal axis 10 of the valve housing 2, the locking pin 23 can be easily transferred by turning the pressure element 9 from the position shown in FIG. 2a to the position shown in FIG. 3a in the bend 25. In this position of the locking pin 23 in the bend 25, the spring element 13 cannot press the pressure element 9 back upwards into the position closing the flow channel 3, even without the compressive force D counteracting the spring force of the spring element 13.

In order to facilitate the rotation of the pressure element 9 for actuating the bayonet lock 22 and also to allow actuation with only one finger, a radially outwardly projecting actuating lever 26 is arranged at the proximal end of the spring-loaded pressure element 9. FIG. 4 shows an embodiment of the actuating lever 26, which is modified with respect to FIGS. 1a, 2a and 3a.

To reclose the flow channel 3 with the valve piston 4, the surgeon must only again rotate the pressure element 9 about the longitudinal axis 10 of the valve housing 2 until the locking pin 23 again disengages from the bend 25, as shown in FIG. 2a. As soon as the surgeon no longer exerts compressive force D on the pressure element 9, the spring element 13 presses the pressure element 9 and thus also the valve piston 4, which is operatively connected with the pressure element 9, back into the position closing the flow channel 3 as per FIG. 1b. In this position, on the one hand, the sealing body 15 again bears against the valve seat 17, sealing off the flow channel 3, and on the other hand, the sealing body 16 no longer bears against the valve seat 18, so that ambient air U can again be drawn in via the air intakes 20.

When actuating the pressure element 9, the pin and slot control 21 allows for a guided displacement of the locking pin 23 in the slotted guide 24.

Even if the locked position of the valve piston 4 is shown in FIGS. 3a and 3b such that it completely releases the flow channel 3, it is of course also possible to lock the pressure element 9 or the valve piston 4 in each intermediate position between the position closing the flow channel 3 and the position releasing the flow channel 3, or also to provide different locking positions on a push button valve 1.

As further seen from the figures, the sealing bodies 15 and 16 of the valve piston 4 are formed as a thickening of the valve piston 4 with conical transition regions. The conical design of the transition areas from the valve piston 4 to the actual sealing bodies 15 and 16 prevents the flow channel 3 from being abruptly closed or opened when adjusting the valve piston 4. Due to the conicity of the sealing bodies 15 and 16, a slow opening and closing of the flow channel 3 is made possible.

The second embodiment for forming the push button valve 1 illustrated in FIGS. 5a to 8c differs from the embodiment shown above in that the pin and slot control 21 is formed as a latching surface 27 and a groove 28, which can be fitted on the latching surface 27.

The groove 28 is thereby formed on the pressure element 9 and the latching surface 27 is formed as a surface arranged on the inside of the pusher housing 12, radially inwardly extending in a semicircular manner.

Figure 5A:
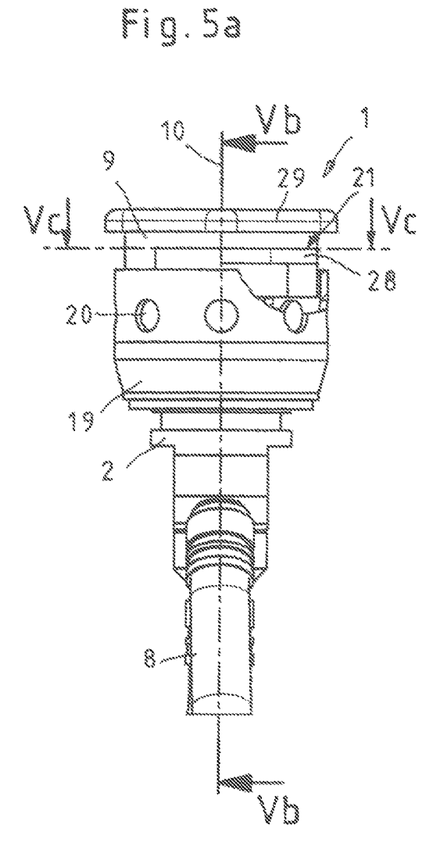
FIG. 5a is a partially cutaway side view of a second embodiment of a push button valve according to the invention, showing the valve in the position closing the flow channel.
Figure 5B:
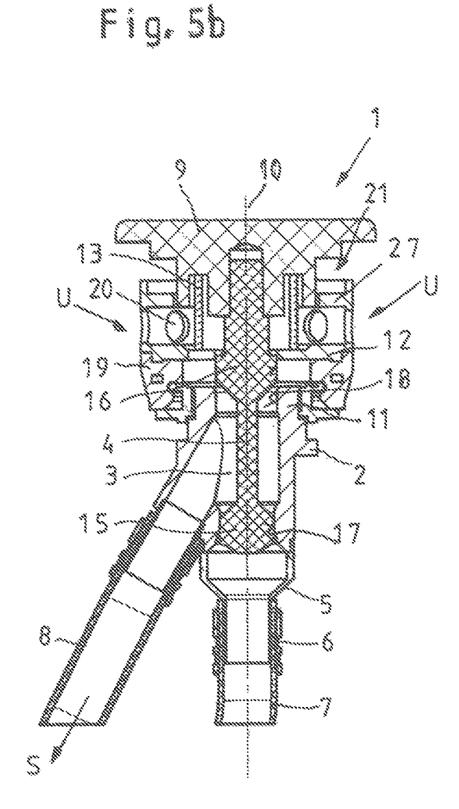
Figure 5C:
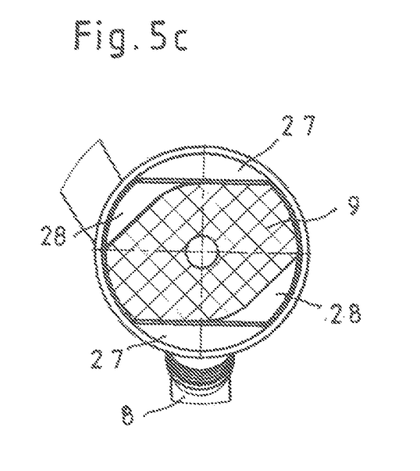

The sectional view of the push button valve 1 shown in FIG. 5b shows the unactuated starting position of the push button valve 1 in which the valve piston 4 completely closes the flow channel 3 formed in the valve housing 2 at the distal end. In this closed position, the sealing body 15 arranged on the end of the valve piston 4 remote from the pressure element 9 radially circumferentially seals off the valve seat 17 formed in the valve housing 2, and thus closes the flow channel 3 in a substantially fluid-tight manner.

Also in this embodiment, air intakes 20 are formed in the pusher housing 12, via which ambient air can be drawn in the direction of the arrow U and discharged via the suction line 8 when the flow channel 3 is closed on the distal side by the valve piston 4.

As can be seen in particular from FIGS. 5c, 6c, 7c and 8c, the pin and slot control 21, via which the pressure element 9 and the pusher housing 12 are coupled together, is designed as a latching surface 27 and a groove 28 which can be fitted on the latching surface 27.

In the position of the push button valve 1 shown in FIGS. 5a and 5b, in which the valve piston 4 is in the position closing off the flow channel 3, the groove 28 formed on the pressure element 9 is arranged above the latching surface 27.

Figure 6A:
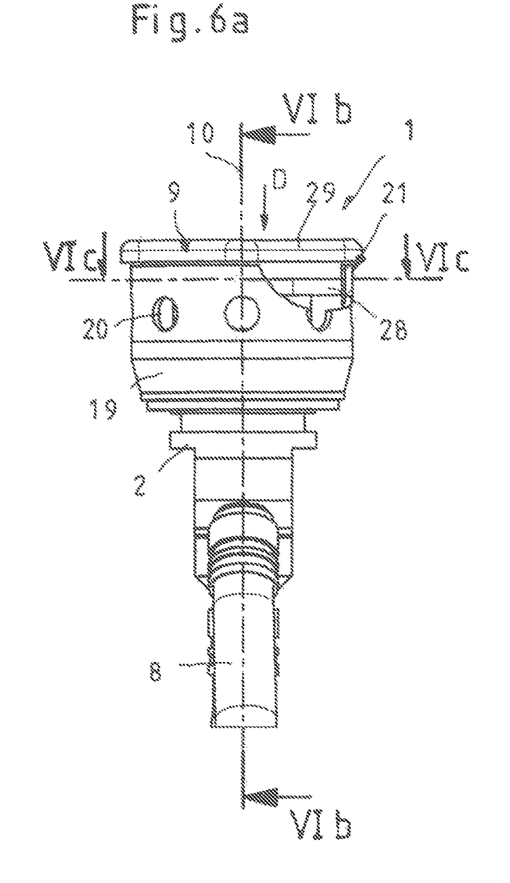
FIG. 6a is a view according to FIG. 5a, but showing the valve in a position releasing the flow channel.
Figure 6B:
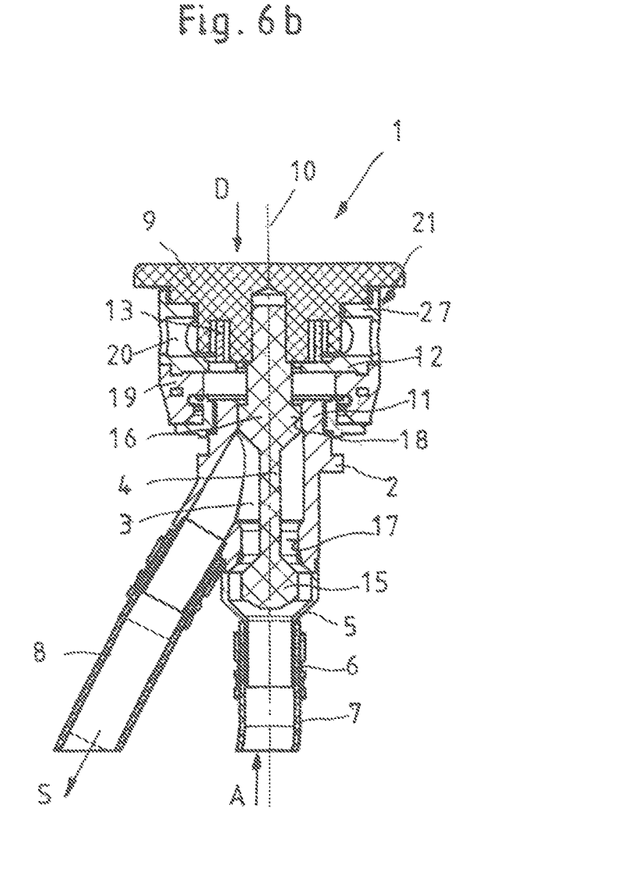

The sectional view of the push button valve 1 shown in FIG. 6b shows the actuated position of the push button valve 1, in which the valve piston 4 completely releases the flow channel 3 formed in the valve housing 2 at the distal end. In this open position, the sealing body 15 of the valve piston 4 is no longer sealingly attached to the valve seat 17 formed in the valve housing 2, but is displaced in the direction of the longitudinal axis 10 of the valve housing 2, away from the valve seat 17 to the distal (in the illustration FIG. 6b, downwards).

The adjustment of the valve piston 4 from the position closing the flow channel 3 shown in FIG. 5b to the position releasing the flow channel 3 shown in FIG. 6b is effected by pressing the spring-loaded pressure element 9 in the direction of the longitudinal axis 10 of the valve housing 2 to the distal (in the illustration of FIG. 6b, downward) with a compressive force D. The axial pressure movement of the pressure element 9 is transmitted without play to the valve piston 4, whereby the sealing body 15 is pressed out of the sealing contact with the valve seat 17.

In this open position of the flow channel 3, the influx of the ambient air U through the air intakes 20 is closed off by the second sealing body 16 of the valve piston 4 arranged close to the pressure element 9, since this sealing body 16 is radially circumferentially sealingly present on the corresponding second valve seat 18 formed in the valve housing 2 when the pressure element 9 is depressed.

Closing the influx of the ambient air U has the effect that the full suction power of the suction line 8 is present at the flow channel 3 and that liquid can be drawn from the patient in the direction of the suction direction indicated by the arrow A via the line 7.

In the position of the push button valve 1 shown in FIG. 6a, in which the valve piston 4 is in the position releasing the flow channel 3, the groove 28 formed on the pressure element 9 lies in the plane that contains the latching surface 27 arranged on the inside of the pusher housing 12.

Since the spring element 13 is arranged such that the pressure element 9 and thus also the valve piston 4 are biased in the position closing the flow channel 3, the surgeon must hold the pressure element 9 down with the compressive force D as long as the suction pressure is to be present at the line 7.

In order to relieve the surgeon, according to the positions of the push button valve 1 shown in FIGS. 7a to 8c, it is possible to lock the pressure element 9 and thus also the valve piston 4 in the position releasing the flow channel 3.

Figure 7A:
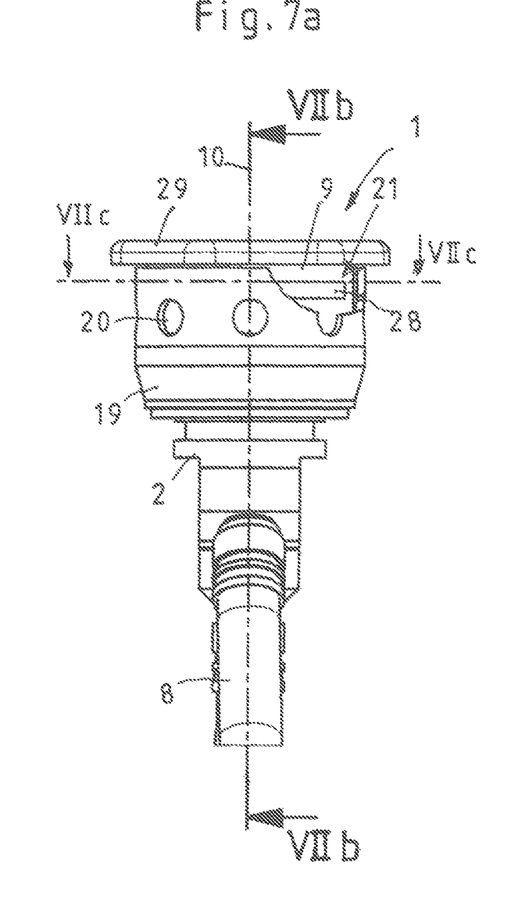
FIG. 7a is a view according to FIG. 6a, but additionally showing the pressure element in an almost completely locked position.
Figure 7B:
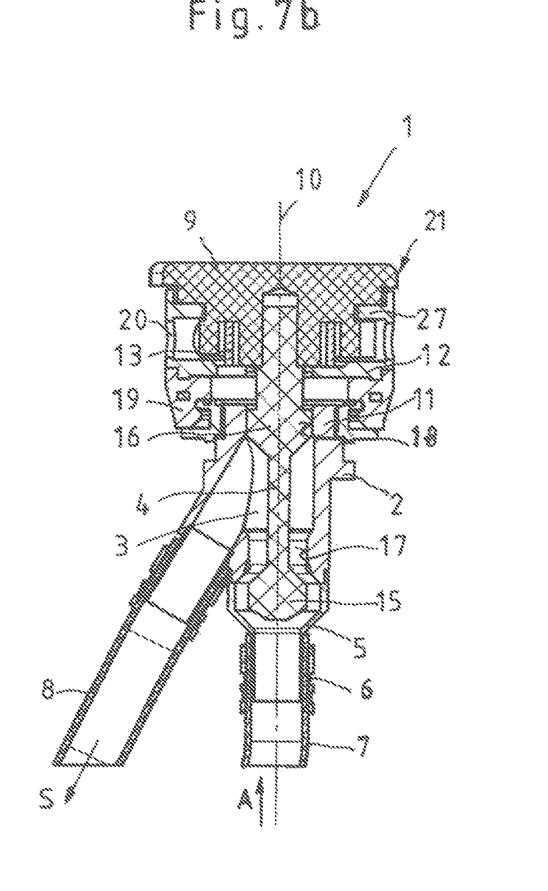
Figure 7C:
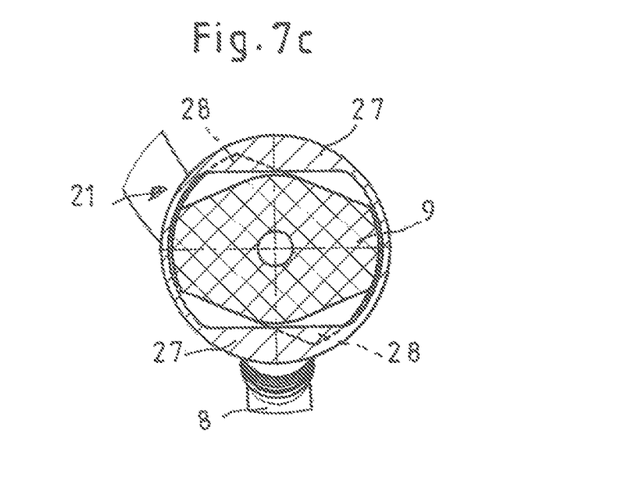
Figure 8A:
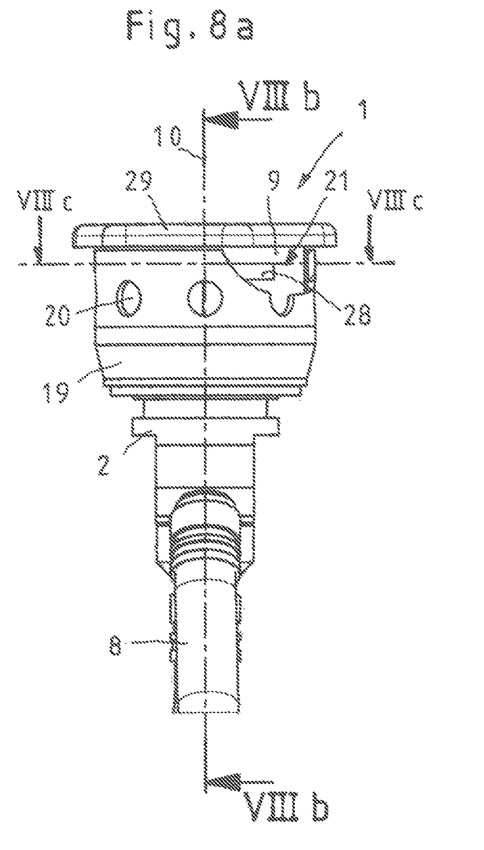
FIG. 8a is a representation according to FIG. 6a, but additionally showing the pressure element in a fully locked position.
Figure 8B:
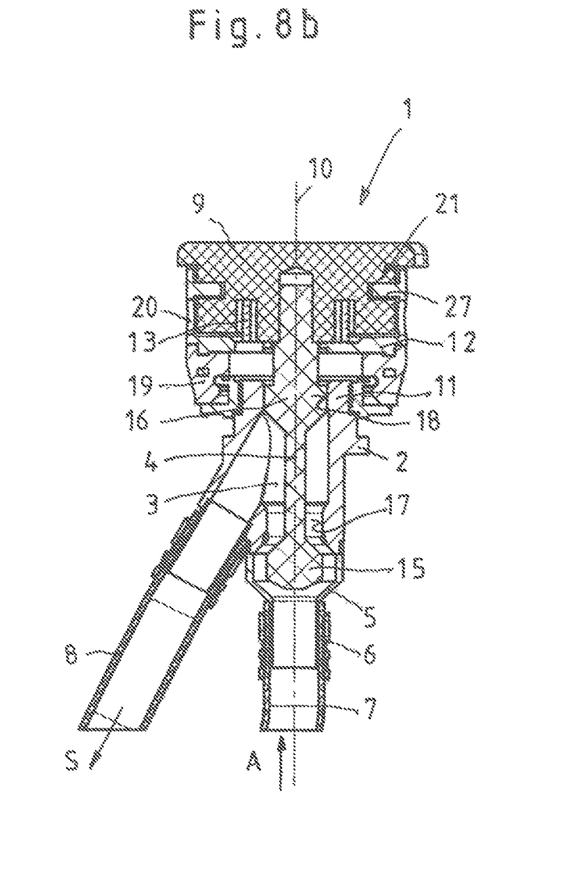
Figure 8C:
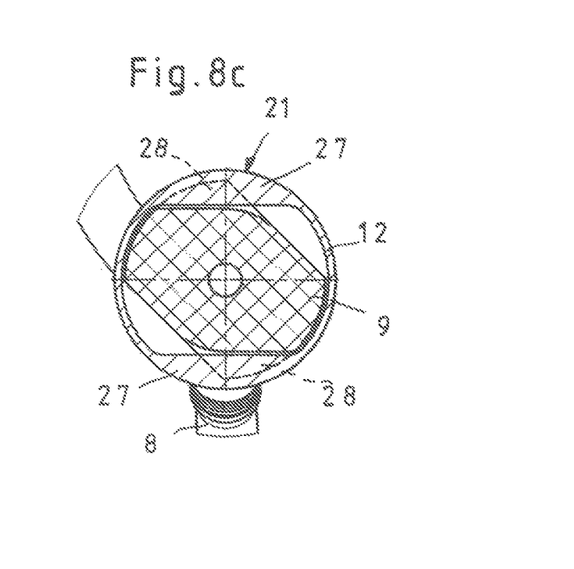

For this purpose, by turning the pressure element 9 about the longitudinal axis 10 of the valve housing 2, the groove 28 formed on the pressure element 9 can be transferred to the positions shown in FIGS. 7c and 8c, in which the latching surface 27 of the pusher housing 12 is lockingly received in the groove 28a. In this position of the latching surface 27 in the groove 28, the spring element 13 cannot press the pressure element 9 back up into the position closing the flow channel 3, even without the compressive force D counteracting the spring force of the spring element 13.

Figure 6C:
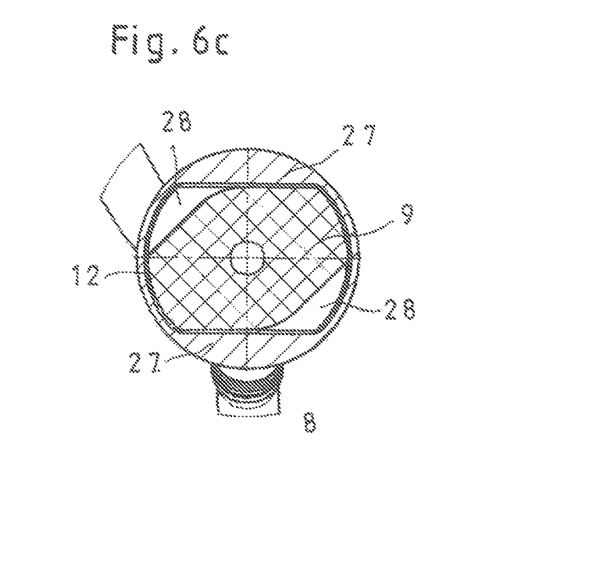

FIGS. 7a to 7c show an intermediate position between the representations according to FIGS. 6a to 6c on the one hand, and FIGS. 8a to 8c on the other hand. These images FIGS. 7a to 7c were taken to better illustrate the trajectory between the groove 28 and the latching surface 27 for locking the pressure element 9.

In order to facilitate the rotation of the pressure element 9 for actuating the pin and slot control 19 and also to allow actuation with only one finger, grip recesses 29 are formed in the outer contour of the proximal end of the spring-loaded pressure element 9.

To reclose the flow channel 3 with the valve piston 4, the surgeon only has to turn the pressure element 9 about the longitudinal axis 10 of the valve housing 2 again until the groove 28 again disengages from the latching surface 27. As soon as the surgeon no longer exerts compressive force D on the pressure element 9, the spring element 13 presses the pressure element 9 and thus also the valve piston 4 back into the position closing the flow channel 3 seen in FIG. 5b.

The push button valves 1 designed as described above are characterized in that they provide the surgeon with a simple and fatigue-free one-handed operation, since the pressure element 9 and the valve piston 4 can be locked in a position releasing the flow channel 3.

The invention being thus described, it will be obvious that the same may be varied in many ways. Such variations are not to be regarded as a departure from the spirit and scope of the invention, and all such modifications as would be obvious to one skilled in the art are to be included within the scope of the following claims.

What is claimed is:

1. A medical push button valve comprising:
   a valve housing;
   a flow channel formed in the valve housing; and
   a valve piston displaceably arranged in the valve housing between a position releasing the flow channel and a position closing the flow channel,
   wherein the valve piston is operatively connected with a pressure element mounted on the valve housing and spring-loaded via at least one spring element, and
   wherein the valve piston is biased via the pressure element in the position closing the flow channel,
   wherein the pressure element is rotatably movable between a locked state and an unlocked state when the valve piston, which is operatively connected with the pressure element, at least partially releases the flow channel and aspirated liquid is suctioned through the flow channel,
   wherein the pressure element is mounted in a pusher housing arranged at a proximal end of the valve housing,
   wherein an elastic locking ring is provided, the elastic locking ring interconnecting the valve housing and the pusher housing, such that the valve housing and the pusher housing remain stationary with respect to one another during movement of the valve piston, and the elastic locking ring being provided on an outer surface of the valve housing and an outer surface of the pusher housing at a transition region from the valve housing to the pusher housing,
   wherein the pressure element is rotatable relative to the pusher housing about a longitudinal axis of the valve housing,
   wherein the pressure element and the pusher housing are coupled together via at least one pin and slot control,
   wherein the at least one pin and slot control is designed as a latching surface and groove,
   wherein the groove is a recessed portion of an exterior surface of the pressure element and the latching surface is formed as a semicircular radially inwardly extending protrusion arranged on an inner surface of the pusher housing,
   wherein when the valve piston is in the position closing the flow channel, the groove is positioned in a different plane than the latching surface,
   wherein when the valve piston is in the position releasing the flow channel and the pressure element is rotated into the unlocked state, the latching surface is positioned in a same plane as the groove but is disposed outside of the groove such that the latching surface opposes a non-recessed portion of the exterior surface of the pressure element, and
   wherein when the valve piston is in the position releasing the flow channel and the pressure element is rotated into the locked state, the latching surface is positioned in the same plane as the groove and the latching surface is slid into and accommodated within the groove to lock the pressure element.

2. The medical push button valve according to claim 1, wherein the pressure element is locked only in the position in which the valve piston operatively connected with the pressure element completely releases the flow channel.

3. The medical push button valve according to claim 1, wherein the at least one spring element is spring-loaded via the pressure element and is integrally formed with the pressure element or the pusher housing.

4. The medical push button valve according to claim 1, wherein, viewed in a direction of a longitudinal axis of the valve housing, the valve piston has two sealing bodies that are formed at a distance from each other and which interact with corresponding valve seats of the valve housing.

5. The medical push button valve according to claim 4, wherein the two sealing bodies of the valve piston are each formed as a thickening of the valve piston with conical transition regions.

6. The medical push button valve according to claim 1, wherein at a proximal end of the pressure element, a radially outwardly projecting actuating lever is arranged.

7. The medical push button valve according to claim 1, wherein grip recesses are formed in an outer contour of a proximal end of the pressure element.

8. The medical push button valve according to claim 1, wherein the pusher housing circumferentially surrounds the pressure element.

9. The medical push button valve according to claim 1, wherein the elastic locking ring directly contacts the outer surface of the valve housing and directly contacts the outer surface of the pusher housing, and wherein the outer surface of the valve housing and the outer surface of the pusher housing face a same direction.

* * * * *